United States Patent
Ehlenz et al.

(10) Patent No.: US 7,544,802 B2
(45) Date of Patent: Jun. 9, 2009

(54) PROCESS FOR THE PREPARATION OF 2-(ETHOXYMETHYL)-TROPANE DERIVATIVES

(75) Inventors: Richard Ehlenz, Bad Kreuznach (DE); Oliver Meyer, Dorsheim (DE); Sascha Wagner, Frei-Laubersheim (DE)

(73) Assignee: Neurosearch A/S, Ballerup (DK)

( * ) Notice: Subject to any disclaimer, the term of this patent is extended or adjusted under 35 U.S.C. 154(b) by 254 days.

(21) Appl. No.: 11/047,260

(22) Filed: Jan. 31, 2005

(65) Prior Publication Data

US 2005/0171145 A1  Aug. 4, 2005

(30) Foreign Application Priority Data

Jan. 31, 2004  (DE)  .................. 10 2004 004 965

(51) Int. Cl.
*C07D 451/02* (2006.01)
*C07D 451/00* (2006.01)

(52) U.S. Cl. ...................... 546/124; 546/125
(58) Field of Classification Search ............... 546/124, 546/125

See application file for complete search history.

(56) References Cited

U.S. PATENT DOCUMENTS

| | | | |
|---|---|---|---|
| 6,288,079 B1 * | 9/2001 | Scheel-Kruger et al. | .... 514/304 |
| 2004/0106643 A1 | 6/2004 | Gouliaev et al. | |
| 2005/0020621 A1 | 1/2005 | Scheel-Krueger et al. | |

FOREIGN PATENT DOCUMENTS

| | | |
|---|---|---|
| WO | WO 97/30997 A1 | 8/1997 |
| WO | WO 02/102801 A1 | 12/2002 |
| WO | WO 03/045388 A1 | 6/2003 |

OTHER PUBLICATIONS

Burakova et al Russian Chemical Bull. Internation Edition vol. 51 No. 10 pp. 1829-1840 (2002).*
Merz, Angew. Chem. Edit. vol. 12 No 10 pp. 846-847 (1973).*

* cited by examiner

*Primary Examiner*—Janet L. Andres
*Assistant Examiner*—Raymond Covington
(74) *Attorney, Agent, or Firm*—Birch, Stewart, Kolasch & Birch, LLP

(57) ABSTRACT

The present invention relates to a process for preparing a 2-(ethoxymethyl)-tropane derivative or a pharmaceutically acceptable salt thereof, by reacting the corresponding 2-(hydroxymethyl)-tropane derivative with ethyl bromide in the presence of a base, and a phase transfer catalyst.

13 Claims, No Drawings

PROCESS FOR THE PREPARATION OF 2-(ETHOXYMETHYL)-TROPANE DERIVATIVES

The present invention relates to an improved process for preparing a 2-(ethoxymethyl)-tropane derivative by reacting a 2-(hydroxymethyl)-tropane derivative with ethyl bromide in the presence of a base and a phase transfer catalyst.

BACKGROUND TO THE INVENTION 2-(ethoxymethyl)-tropane derivatives are valuable pharmaceutical active substances for the treatment of various central nervous disorders, such as, e.g., Parkinson's or Alzheimer's disease.

According to the teaching of International Publication No. WO9730997, which is incorporated by reference herein in its entirety, 2-(ethoxymethyl)-tropane derivatives are prepared either from a 2-(tosylmethyl)-tropane derivative by reacting with ethoxide, or by reacting a 2-(hydroxymethyl)-tropane derivative with sodium hydride as base and diethylsulphate. For safety reasons, production on an industrial scale using sodium hydride is virtually impossible. Moreover, this ethoxylation is not really reproducible, the reaction times are long, and the active substance is produced in unsatisfactory yields as a solid, which is difficult to isolate.

Thus, an object underlying the present invention is to provide a process that enables 2-(ethoxymethyl)-tropane derivatives to be produced in good yields on a large industrial scale, while avoiding the disadvantages that occur with the processes known from the prior art.

DETAILED DESCRIPTION OF THE INVENTION

Surprisingly, it has now been found that 2-(ethoxymethyl)-tropane derivatives of formula (I) or a pharmaceutically acceptable salt thereof,

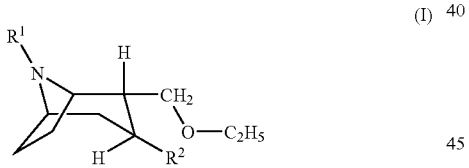

(I)

wherein $R^1$ denotes hydrogen or $C_{1-6}$ alkyl, particularly methyl; and $R^2$ denotes phenyl optionally mono- or polysubstituted by halogen, trifluoromethyl or cyano, particularly 3,4-dichlorophenyl; may be prepared in good yields and on an industrial scale by reacting a 2-(hydroxymethyl)-tropane derivative of formula (II),

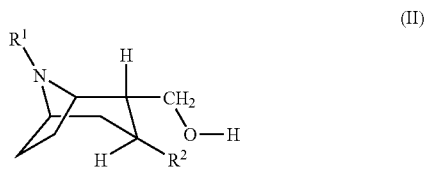

(II)

wherein $R^1$ and $R^2$ are defined as for formula (I), with ethyl bromide in the presence of a base, a phase transfer catalyst, and, optionally, a diluent.

Thus, the invention relates to an improved process for preparing a 2-(ethoxymethyl)-tropane derivative of formula (I) or a pharmaceutically acceptable salt thereof, in which a 2-(hydroxymethyl)-tropane derivative of formula (II) is reacted with ethyl bromide in the presence of a base, a phase transfer catalyst, and, optionally, a diluent, and then, optionally, treated with an acid.

Preferred embodiments of the process according to the invention are processes wherein:

(A) an alkali metal hydroxide, such as for example lithium hydroxide, sodium hydroxide, or potassium hydroxide, particularly powdered potassium hydroxide, is used as base;

(B) the phase transfer catalyst (PTC) used is a tetraalkylammonium or tetraalkylphosphonium salt, while the alkyl groups may be identical or different, such as, for example, salts of tetraoctylammonium, methyltrioctyl ammonium, tetramethylammonium, tetraethylammonium, tetrahexylammonium, Aliquat 175 (tributylmethylammonium), or Aliquat 336 (methyltrioctylammonium). Preferably the PTC is a tetraalkylammonium halide, a tetraalkylammonium sulphate, a tetraalkylammonium hydrogen sulphate, a tetraalkylammonium nitrate, or a tetraalkylammonium phosphate, particularly a tetraalkylammonium hydrogen sulphate, most particularly, preferably, tetra-n-butylammonium hydrogen sulphate.

The term "alkyl," as used above and hereinafter in relation to the phase transfer catalyst, includes straight-chain and branched alkyl groups with 1 to 8, preferably 2 to 6, and particularly 4 carbon atoms. Preferred alkyl groups, which may be mentioned, are, thus, ethyl, n-propyl, i-propyl, n-butyl, 2-butyl, tert-butyl, n-pentyl, 2-pentyl, neo-pentyl, n-hexyl- and 2-hexyl group. The n-butyl group is most particularly preferred.

Other preferred embodiments of the process according to the invention are processes wherein:

(C) the diluent used is an aromatic hydrocarbon, preferably benzene, toluene, or xylene, particularly toluene, or an optionally halogenated aliphatic hydrocarbon, preferably cyclohexane, methylcyclohexane, dichloromethane, chloroform, carbon tetrachloride, or dichloroethane, particularly dichloromethane, or an ether, preferably tetrahydrofuran (THF), diethyl ether, diisopropylether, tert-butylmethylether (TBME), or 1,2-dimethoxyethane (DME), particularly 1,2-dimethoxyethane;

(D) the reaction is carried out at temperatures in the range from about −10° C. to about 90° C., preferably from about 0° C. to about 80° C., and particularly from about 20° C. to about 65° C.;

(E) about 0.75 to about 100 equivalents, preferably about 1.5 to about 5.5 equivalents, and particularly about 4 equivalents of ethyl bromide, are used to about 1 equivalent of a compound of formula (II);

(F) about 2.5 to about 100 equivalents, preferably about 3.8 to about 10.5 equivalents, particularly about 7.5 to about 8.5 equivalents, of base are used to about 1 equivalent of a compound of formula (II);

(G) about 0.01 to about 0.5 equivalents, preferably about 0.02 to about 0.2 equivalents, particularly about 0.05 to about 0.15 equivalents, of phase transfer catalyst are used to about 1 equivalent of a compound of formula (II);

(H) after the end of the reaction, water is added to the reaction mixture, the organic and aqueous phases are separated, the organic phase is washed with water, evaporated down under reduced pressure, and the residue is treated with an acid and the acid addition salt obtained is isolated;

(I) the active substance of formula (I) obtained is treated with an inorganic or organic acid treated. The resulting acid addition salts are, for example, hydrochlorides, hydrobromides, phosphates, nitrates, perchlorates, sulphates, citrates, lactates, tartrates, maleates, fumarates, mandelates, benzoates, ascorbates, cinnamates, benzenesulphonates, methanesulphonates, stearates, succinates, glutamates, glycollates, toluene-p-sulphonates, formates, malonates, naphthalene-2-sulphonates, salicylates, and acetates. The citrates are particularly preferred. These salts are prepared using correspondingly well-known production methods.

In a particularly preferred embodiment, 4 equivalents of ethyl bromide, optionally dissolved in 1,2-dimethoxyethane, are metered into a mixture of 1 equivalent of a compound of formula (II), about 20 times as much, by weight, of 1,2-dimethoxyethane based on (II), about 8 equivalents of KOH, and about 0.1 equivalents of tetra-n-butylammonium hydrogen sulphate within 5 to 60 minutes at a temperature between 20 and 35° C., with stirring. After the addition has ended, the mixture is stirred for 30 to 300, preferably about 45 to 180 minutes, at a temperature between 40 and 80° C. Then water is added, and, at the temperature specified, the mixture is stirred for a further 30 to 300, preferably about 45 to 180 minutes, and then the organic phase is separated from the aqueous phase. The organic phase is evaporated down and the residue is treated with an acid, preferably citric acid.

The acid addition salt of the compound of formula (I) is isolated and dried.

Other advantageous aspects of the procedure according to the invention are the high space-time yield of the present process and the high yield and purity of the compound of formula (I) or its salt obtained without any further purification processes. The Examples that follow serve to illustrate processes carried out by way of example for preparing a compound of formula (I). They should be understood as being possible procedures illustrate by way of example without restricting the invention to their content.

EXAMPLE 1

(1R,2R,3S)-2-ethoxymethyl-3-(3,4-dichlorophenyl)-tropane citrate 14.6 g (0.134 mol) of ethyl bromide is metered into a mixture of 10 g (0.0333 mol) (1R,2R,3S)-2-hydroxymethyl-3-(3,4-dichlorophenyl)-tropane (prepared according to WO9730997), 14.92 g powdered (0.266 Mol KOH) caustic potash, 1.16 g (0.00334 mol) of tetra-n-butylammonium hydrogen sulphate, and 200 ml DME within 15 minutes at a temperature of between 20 and 31° C., with stirring.

After the addition has ended the mixture is stirred for 1.5 hours at a temperature between 58 and 62° C., Then 76 ml of water are added, the mixture is stirred for another hour at this temperature and the organic phase is separated off. The organic phase is evaporated down using the rotary evaporator under reduced pressure. The residue is dissolved with 90 ml acetone at 55° C., filtered and rinsed with 10 ml acetone. The solution obtained is treated with a mixture of 6.4 g (0.0333 mol) of citric acid and 20 ml of methanol at 40° C. The crystal suspension is cooled to 20° C. and stirred for one hour at 15 to 20° C. The obtained crystals are isolated and washed with 33 ml acetone. After drying in the vacuum drying cupboard at 40° C.

14.55 g (83.6% of theory) of the title compound are obtained as yellowish crystals with a purity of more than 99.4%.

EXAMPLE 2

(1R,2R,3S)-2-ethoxymethyl-3-(3,4-dichlorophenyl)-tropane citrate 17.5 g (0.161 mol) of ethyl bromide dissolved in 20 ml of 1,2-dimethoxyethane are metered, within 15 minutes, into a mixture of 12 g (0.0400 mol) of (1R,2R,3S)-2-hydroxymethyl-3-(3,4-dichlorophenyl)-tropane (prepared according to WO9730997), 17.9 g of powdered (0.320 mol KOH) caustic potash, 1.39 g (0.00409 mol) of tetra-n-butylammonium hydrogen sulphate, and 220 ml DME at a temperature between 20 and 31° C., with stirring.

After the addition has ended, the mixture is stirred for 1.5 hours at a temperature between 58 and 62° C. Then 76 ml of water are added, the mixture is stirred for another hour at this temperature, and the organic phase is separated off. The organic phase is evaporated down under reduced pressure using the rotary evaporator. The residue is dissolved with 108 ml acetone at 55° C., filtered and rinsed with 40 ml acetone. The solution obtained is treated with a mixture of 7.68 g (0.0400 mol) of citric acid and 24 ml of methanol at 40° C. The crystal suspension is cooled to 20° C. and stirred for one hour at 15 to 20° C. The crystals obtained are isolated and washed with at least 80 ml acetone. After drying in the vacuum drying cupboard at 40° C.

17.44 g (83.85% of theory) of the title compound are obtained as yellowish crystals with a purity of more than 99.5%.

EXAMPLE 3

(1R,2R,3S)-2-ethoxymethyl-3-(3,4-dichlorophenyl)-tropane citrate

This example is a process according to International Publication No. WO9730997. This example is provided as a comparason to the process according to the present invention.

Sodium hydride (60% in oil) (4.6 g, 0.12 mol) and ethylsulphate (15.7 ml, 0.12 mol) are added to a mixture of (1R,2R,3S)-2-hydroxymethyl-3-(3,4-dichlorophenyl)tropane (26.9 g, 0.09 mol) and THF (200 ml) and heated to 30-40° C. for half an hour. The reaction mixture is stirred overnight at ambient temperature, then heated to 30-40° C. for half an hour and poured into 500 ml of water. The mixture is extracted twice with TBDME, the organic phases are washed with water and dried over MgSO₄.32.82 g of the base are obtained.

Citric acid (19.2 g, 0.1 mol) is added to a solution of the resulting (1R,2R,3S)-2-ethoxymethyl-3(3,4-dichlorophenyl) tropane in 96% ethanol (275 ml). The solution is refluxed and left to stand for 3 hours at ambient temperature in order to crystallise. The mixture is placed over an ice bath for half an hour, the crystalline product is filtered off and washed with 96% ethanol (50 ml and 25 ml). After drying 32.85 g (70% of theory) of the title compound is obtained with a melting point of 153-155.5° C.

What is claimed is:
1. A process for the preparation of 2-(ethoxymethyl)-tropane compounds comprising:
   providing a 2-(hydroxymethyl)-tropane compound of formula (II)

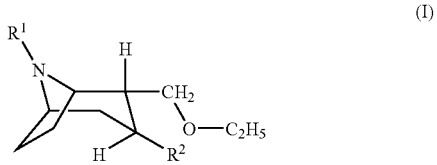

(I)

wherein R¹ denotes methyl and R² denotes 3,4-dichlorophenyl;
providing ethyl bromide, a base, and a phase-transfer catalyst; and
reacting a reaction mixture comprising the 2-(hydroxymethyl)-tropane compound, ethyl bromide, the base, and the phase-transfer catalyst to generate a 2-(ethoxymethyl)-tropane compound of formula (I) or a pharmaceutically acceptable salt thereof,

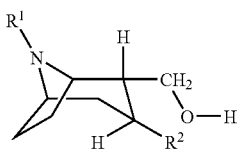

(II)

wherein R¹ and R² are defined as for formula (II);
and wherein the base is potassium hydroxide; and wherein the phase-transfer catalyst is a tetraalkylammonium hydrogen sulphate.

2. The process according to claim 1, wherein the phase-transfer catalyst is tetra-n-butylammonium hydrogen sulphate.

3. The process according to claim 1, wherein the reaction mixture further comprises a diluent.

4. The process according to claim 3, wherein the diluent is selected from the group consisting of aromatic hydrocarbons, aliphatic hydrocarbons, halogenated aliphatic hydrocarbons, ethers, and mixtures thereof.

5. The process according to claim 3, wherein the diluent is selected from the group consisting of toluene, cyclohexane, methylcyclohexane, dichloromethane, chloroform, carbon tetrachloride, dichloroethane, tetrahydrofluran, diethyl ether, diisopropylether, tert-butylmethylether, 1,2-dimethoxyethane, and mixtures thereof.

6. The process according to claim 1, wherein the reaction step is carried out at a temperature from about −10° C. to about 90° C.

7. The process according to claim 1, wherein the ethyl bromide is metered into a mixture comprising the 2-(hydroxymethyl)-tropane compound, the base, and the phase-transfer catalyst within 5 to 180 minutes to obtain the reaction mixture, and wherein the reaction mixture is stirred for about 30 to about 180 minutes.

8. The process according to claim 1, wherein ethyl bromide is provided in an amount of about 0.75 to about 100 equivalents, and wherein the 2-(hydroxymethyl)-tropane compound is provided in an amount of about 1 equivalent.

9. The process according to claim 1, wherein base is provided in an amount of about 2.5 to about 100 equivalents, and wherein the 2-(hydroxymethyl)-tropane compound is provided in an amount of about 1 equivalent.

10. The process according to claim 1, wherein the phase-transfer catalyst is provided in an amount of about 0.01 to about 0.5 equivalents, and wherein the 2-(hydroxymethyl)-tropane compound is provided in an amount of about 1 equivalent.

11. The process according to claim 1, further comprising:
adding water to the reaction mixture after generating the 2-(ethoxymethyl)-tropane compound to create an organic phase and an aqueous phase, wherein the organic phase comprises the 2-(ethoxymethyl)-tropane compound;
separating the organic and aqueous phases;
washing the organic phase with water;
evaporating the organic phase under reduced pressure to isolate a residue comprising the 2-(ethoxymethyl)-tropane compound;
treating the residue with an acid to obtain an acid addition salt of the 2-(ethoxymethyl)-tropane compound;
isolating the acid addition salt of the 2-(ethoxymethyl)-tropane compound.

12. A process for the preparation of a 2-ethoxymethyl)-tropane compound comprising:
metering 14.6 g (0.134 mol) of ethyl bromide into a mixture of about 10 g (0.0333 mol) (1R,2R,3S)-2-hydroxymethyl-3-(3, 4-dichlorophenyl)-tropane, 14.92 g powdered (0.266 Mol KOH) caustic potash, 1.16 g (0.00334 mol) of tetra-n-butylammonium hydrogen sulphate, and 200 ml DME within 15 minutes at a temperature of between 20 and 31° C., with stirring;
stirring the mixture for 1.5 hours at a temperature between 58 and 62° C.;
adding 76 ml of water to the mixture and stirring the mixture for 1 hour at a temperature between 58 and 62° C., whereby an organic phase and an aqueous phase are generated;
separating the organic phase from the aqueous phase;
evaporating down the organic phase using a rotary evaporator under reduced pressure to isolate a residue;
dissolving the residue with 90 ml acetone at 55° C., filtering the residue, and rinsing the residue with 10 ml acetone to obtain a solution;
treating the obtained solution with a mixture of 6.4 g (0.0333 mol) of citric acid and 20 ml of methanol at 40° C. to obtain a crystal suspension;
cooling the obtained crystal suspension to 20° C. and stirring the crystal suspension for 1 hour at 15 to 20° C. to obtain crystals;
isolating the obtained crystals;
washing the crystals with 33 ml acetone; and
drying the crystals in a vacuum drying cupboard at 40° C., whereby 14.55 g of (1R,2R,3S)-2-ethoxymethyl-3-(3,4-dichlorophenyl)-tropane citrate is obtained as yellowish crystals with a purity of more than 99.4%.

13. A process for the preparation of a 2-(ethoxymethyl)-tropane compound comprising:
metering 17.5 g (0.161 mol) of ethyl bromide dissolved in 20 ml of 1,2-dimethoxyethane within 15 minutes into a mixture of 12 g (0.0400 mol) of(1R,2R,3S)-2-hydroxymethyl-3-(3,4-dichlorophenyl)-tropane, 17.9 g of powdered (0.320 mol KOH) caustic potash, 1.39 g (0.00409 mol) of tetra-n-butylammonium hydrogen sulphate, and 220 ml DME, at a temperature between 20 and 31° C., with stirring;
stirring the mixture for 1.5 hours at a temperature between 58 and 62° C.;
adding 76 ml of water, and stirring the mixture for 1 hour at a temperature between 58 and 62° C., whereby an organic phase and an aqueous phase are generated;
separating the organic phase from the aqueous phase;
evaporating down the organic phase under reduced pressure using a rotary evaporator to obtain a residue;
dissolving the obtained residue with 108 ml acetone at 55° C., filtering the residue, and
rinsing the residue with 40 ml acetone to obtain a solution;
treating the obtained solution with a mixture of 7.68 g (0.0400 mol) of citric acid and 24 ml of methanol at 40° C. to obtain a crystal suspension;
cooling the obtained crystal suspension to 20° C. and stirring for one hour at 15 to 20° C. to obtain crystals;
isolating the obtained crystals;
washing the crystals with at least 80 ml acetone;
drying the crystals in a vacuum drying cupboard at 40° C., whereby 17.44 g of (1R,2R,3S)-2-ethoxymethyl-3-(3,4-dichlorophenyl)-tropane citrate is obtained as yellowish crystals with a purity of more than 99.5%.

* * * * *